United States Patent
Johnson

(10) Patent No.: US 7,868,200 B2
(45) Date of Patent: Jan. 11, 2011

(54) PROCESS FOR PREPARING ALICYCLIC CARBOXYLIC ACID COMPOUNDS

(75) Inventor: Walter E. Johnson, Jacksonville, FL (US)

(73) Assignee: LyondellBasell Flavors & Fragrances, LLC, Houston, TX (US)

( * ) Notice: Subject to any disclaimer, the term of this patent is extended or adjusted under 35 U.S.C. 154(b) by 257 days.

(21) Appl. No.: 12/317,878

(22) Filed: Dec. 30, 2008

(65) Prior Publication Data
US 2010/0168470 A1    Jul. 1, 2010

(51) Int. Cl.
C07C 61/08 (2006.01)
(52) U.S. Cl. .................................. 562/400
(58) Field of Classification Search .............. None
See application file for complete search history.

(56) References Cited

U.S. PATENT DOCUMENTS

| | | | |
|---|---|---|---|
| 3,911,037 | A | 10/1975 | Blackmar et al. |
| 4,157,384 | A | 6/1979 | Watson et al. |
| 4,759,881 | A | 7/1988 | Lang et al. |
| 5,162,586 | A | 11/1992 | Villacorta et al. |
| 5,318,710 | A | 6/1994 | Campbell |
| 5,910,605 | A | 6/1999 | Cosmo et al. |
| 6,054,628 | A | 4/2000 | Stroezel et al. |
| 6,147,217 | A | 11/2000 | Senanayake et al. |
| 6,365,773 | B1 | 4/2002 | Cheng et al. |
| 6,458,985 | B1 | 10/2002 | Holmes et al. |
| 7,034,187 | B2 | 4/2006 | Parthiban |
| 2002/0058286 | A1 | 5/2002 | Danishefsky et al. |
| 2006/0167305 | A1 | 7/2006 | Yokoyama |

FOREIGN PATENT DOCUMENTS

| | | |
|---|---|---|
| EP | 73569 | 3/1983 |
| GB | 1392907 | 5/1975 |
| JP | 60-181065 | 9/1985 |
| JP | 2000-226393 | 8/2000 |
| JP | 2005-068062 | 3/2005 |

OTHER PUBLICATIONS

X. Yin et al., "Recent developments in the activation of carbon dioxide by metal complexes," *Coordination Chemistry Reviews*, vol. 181, p. 27-59 (1999).

M. Erman, "Cooling Compounds," *Presentation to the Society of Flavor Chemists*, Millennium Specialty Chemicals, p. 1-59 (Dec. 4, 2003).

*Primary Examiner*—Paul A Zucker
(74) *Attorney, Agent, or Firm*—Jarrod N. Raphael

(57) ABSTRACT

A process for preparing at least one alicyclic carboxylic acid compound by Grignard reaction, the process comprising:
reacting magnesium and at least one alicyclic halide compound in at least one solvent to produce at least one alicyclic Grignard reagent;
concurrently adding carbon dioxide to the magnesium, the alicyclic halide compound, the solvent, and the alicyclic Grignard reagent, while the alicyclic Grignard reagent is still being produced, to form at least one alicyclic carboxylate magnesium salt; and
hydrolyzing the alicyclic carboxylate magnesium salt to form the alicyclic carboxylic acid compound;
wherein the alicyclic Grignard reagent and the alicyclic carboxylate magnesium salt are prepared in a one-pot synthesis.

16 Claims, No Drawings

US 7,868,200 B2

PROCESS FOR PREPARING ALICYCLIC CARBOXYLIC ACID COMPOUNDS

FIELD OF INVENTION

The present inventive subject matter generally relates to a novel process for preparing alicyclic carboxylic acid compounds.

BACKGROUND OF INVENTION

Compositions having a physiological cooling effect are well known in the art. In particular, menthol, which is an alicyclic alcohol, is well known for its physiological cooling effect on the skin and mucous membranes of the mouth, and has been used extensively as a flavoring agent in foodstuffs and beverages, as well as generally in the flavor and fragrance industry. However, although menthol demonstrates an intense cooling effect, menthol also has several disadvantages, including high volatility, strong smell, bitter taste, can produce a burning sensation in high concentrations, and can interfere with other compositions. Accordingly, other physiological coolants derived from menthol have been synthesized in order to try to overcome the deficiencies of menthol.

For example, U.S. Pat. No. 4,157,384 discloses 3-substituted-p-menthanes in which the compositions therein have a carbon-carbon bond in the third position, as opposed to the carbon-hydroxyl bond in menthol. The compounds disclosed in U.S. Pat. No. 4,157,384 are generally known as WS-type coolants, and are generally derived from key synthetic intermediate p-menthane-3-carboxylic acid, which is an alicyclic carboxylic acid compound also known as WS-1.

Synthesis of p-menthane-3-carboxylic acid is also well known in the art, and a process for producing p-menthane-3-carboxylic acid is disclosed in GB 1,392,907. In particular, GB 1,392,907 discloses a process for producing p-menthane-3-carboxylic acid by conventional Grignard reaction techniques, including reacting p-menth-3-yl chloride and magnesium to produce the corresponding Grignard reagent, and then after the Grignard reagent is fully produced, reacting the Grignard reagent with carbon dioxide to produce the corresponding carboxylate magnesium salt (i.e., Grignard reagent/carbon dioxide complex). The carboxylate magnesium salt is then hydrolyzed in acid to produce the resulting alicyclic carboxylic acid compound, p-menthane-3-carboxylic acid.

Although the process of GB 1,392,907 can result in producing p-menthane-3-carboxylic acid (i.e., WS-1), which can then be used as an intermediate to produce other WS-type coolants, the process of GB 1,392,907 has several disadvantages. In particular, the process of GB 1,392,907 is carried out by conventional Grignard reaction techniques in which the menthyl halide is first reacted with magnesium to produce the Grignard reagent, and then, only after all of the menthyl halide is added and reacted to produce the Grignard reagent, the Grignard reagent is then reacted with carbon dioxide to produce the carboxylate magnesium salt. Thereafter, the carboxylate magnesium salt is then hydrolyzed to liberate the carboxylic acid product. Therefore, one of the major disadvantages of the process of GB 1,392,907 is that the process is carried out in multiple separate steps, including first fully producing the Grignard reagent from the reaction between the menthyl halide and magnesium. Then, only after all of the menthyl halide has been added and reacted with the magnesium to produce all of the resultant Grignard reagent, is the Grignard reagent then reacted with carbon dioxide to produce the carboxylate magnesium salt, which is then hydrolyzed to produce the resultant carboxylic acid product. This demarcation of steps between producing all of the Grignard reagent first, and then only after all of the Grignard reagent is produced, reacting the Grignard reagent with carbon dioxide to produce the resultant carboxylate magnesium salt, not only increases the time required to ultimately produce the resultant alicyclic carboxylic acid product, but also increases the amount and complexity of apparatuses required to run the reaction to completion. In fact, many times multiple reaction vessels are required to first produce the Grignard reagent, and then to separately react the Grignard reagent with carbon dioxide to produce the carboxylate magnesium salt.

Accordingly, there remains a need in the art for a process for preparing alicyclic carboxylic acid compounds, whereby the demarcation of steps between first, fully producing the alicyclic Grignard reagent, and then, only after the alicyclic Grignard reagent is fully produced, reacting the alicyclic Grignard reagent with carbon dioxide to produce the corresponding alicyclic carboxylate magnesium salt, is reduced. In particular, there remains a need in the art for a process for preparing alicyclic carboxylic acid compounds, whereby carbon dioxide is concurrently added to a Grignard reaction mixture comprising an alicyclic halide compound, magnesium, and an alicyclic Grignard reagent, while the alicyclic Grignard reagent is still being produced, to produce an alicyclic carboxylate magnesium salt, with the alicyclic Grignard reagent and the alicyclic carboxylate magnesium salt being prepared in a one-pot synthesis (i.e., in a single reaction vessel).

SUMMARY OF INVENTION

The present inventive subject matter generally relates to a process for producing alicyclic carboxylic acid compounds. In this regard, an embodiment of the present inventive subject matter relates to a process for preparing at least one alicyclic carboxylic acid compound by Grignard reaction, the process comprising:

reacting magnesium and at least one alicyclic halide compound in at least one solvent to produce at least one alicyclic Grignard reagent;

concurrently adding carbon dioxide to the magnesium, the alicyclic halide compound, the solvent, and the alicyclic Grignard reagent, while the alicyclic Grignard reagent is still being produced, to form at least one alicyclic carboxylate magnesium salt; and hydrolyzing the alicyclic carboxylate magnesium salt to form the alicyclic carboxylic acid compound;

wherein the alicyclic Grignard reagent and the alicyclic carboxylate magnesium salt are prepared in a one-pot synthesis.

DETAILED DESCRIPTION OF INVENTION

The novel process of the present inventive subject matter allows for the production of alicyclic carboxylic acid compounds. As discussed above, alicyclic carboxylic acid compounds can be produced by conventional Grignard reactions in which the process entails three separate and distinct steps: (i) an alicyclic halide compound is reacted with magnesium to produce the corresponding alicyclic Grignard reagent; (ii) then, only after all of the alicyclic halide compound is reacted with the magnesium to produce the corresponding alicyclic Grignard reagent, is the alicyclic Grignard reagent then reacted with carbon dioxide to produce the alicyclic carboxylate magnesium salt; and (iii) the alicyclic carboxylate magnesium salt is then hydrolyzed to produce the corresponding alicyclic carboxylic acid compound. However, conventional Grignard processes for producing alicyclic carboxylic acid compounds not only require the alicyclic Grignard reagent to be completely produced before reacting the alicyclic Grignard reagent with carbon dioxide, which requires an abundance of time to perform the two separate and distinct process steps, but also can require multiple reaction vessels to carry out the two separate steps.

Contrastingly, the process of the present inventive subject matter allows for a process for preparing alicyclic carboxylic acid compounds by a Grignard reaction, the process comprising:

reacting magnesium and at least one alicyclic halide compound in at least one solvent to produce at least one alicyclic Grignard reagent;

concurrently adding carbon dioxide to the magnesium, the alicyclic halide compound, the solvent, and the alicyclic Grignard reagent, while the alicyclic Grignard reagent is still being produced, to form at least one alicyclic carboxylate magnesium salt; and hydrolyzing the alicyclic carboxylate magnesium salt to form at least one alicyclic carboxylic acid compound, wherein the alicyclic Grignard reagent and the alicyclic carboxylate magnesium salt are prepared in a one-pot synthesis. Accordingly, the process of the present inventive subject matter can not only allow for the production of the alicyclic Grignard reagent and the alicyclic carboxylate magnesium salt in a one-pot synthesis (i.e., a single reaction vessel), which can minimize the production apparatuses required to perform the present process, but also can reduce the time required to produce the alicyclic carboxylic acid compounds by allowing for the concurrent addition of carbon dioxide to the alicyclic halide compound, magnesium, and alicyclic Grignard reagent, while the production of the alicyclic Grignard reagent is still being produced.

Alicyclic Carboxylic Acid Compounds:

Various alicyclic carboxylic acid compounds can be prepared by the present process. In particular embodiments of the present process, the alicyclic carboxylic acid compounds can generally have at least one $C_3$-$C_8$ all-carbon ring, and may be substituted. In particularly preferred embodiments of the present process, the alicyclic carboxylic acid compounds can generally have at least one $C_4$-$C_6$ all-carbon ring, and may be substituted.

In further preferred embodiments, the alicyclic carboxylic acid compounds can be menthol derivatives, and in particular, can be p-menthane carboxylic acid compounds. Preferred p-menthane carboxylic acid compounds can generally have formula (I):

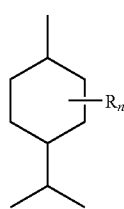

(I)

wherein:
R is COOH or a $C_2$-$C_{10}$ aliphatic group comprising at least one carboxylic acid moiety, wherein the $C_2$-$C_{10}$ aliphatic group is optionally substituted with at least one $C_1$-$C_{10}$ alkyl, $C_2$-$C_{10}$ alkene, $C_2$-$C_{10}$ alkynyl, and combinations thereof; and
n is 1 to 4.

In certain embodiments of the present subject matter, the p-menthane carboxylic acid compounds can be substituted at the third carbon on the cyclohexyl group, and can generally have formula (II):

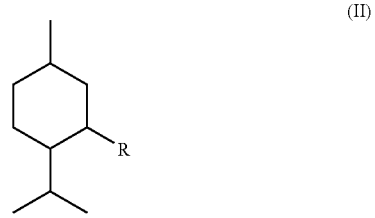

(II)

wherein:
R is COOH or a $C_2$-$C_{10}$ aliphatic group comprising at least one carboxylic acid moiety, wherein the $C_2$-$C_{10}$ aliphatic group is optionally substituted with at least one $C_1$-$C_{10}$ alkyl, $C_2$-$C_{10}$ alkene, $C_2$-$C_{10}$ alkynyl, and combinations thereof; and
n is 1 to 4.

In particularly preferred embodiments of the present process, the alicyclic carboxylic acid compounds are p-menthane carboxylic acid compounds, including, but not limited to, p-menthane-3-carboxylic acid.

In order to prepare the alicyclic carboxylic acid compounds described above, at least one alicyclic halide compound is reacted with magnesium to produce the corresponding alicyclic Grignard reagent. Various alicyclic halides can be used in the present process. In preferred embodiments of the present process, the alicyclic halides can be menthol-halide derivatives, and in particular, can be p-menthane halides. Preferred p-menthane halides can generally have formula (III):

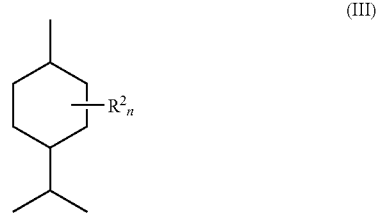

(III)

wherein:
$R^2$ is a halogen or a $C_1$-$C_9$ aliphiatic group comprising at least one halide moiety, wherein the $C_1$-$C_9$ aliphiatic group is optionally substituted with at least one $C_1$-$C_{10}$ alkyl, $C_2$-$C_{10}$ alkene, $C_2$-$C_{10}$ alkynyl, and combinations thereof; and
n is 1 to 4.

In particular embodiments of the present subject matter, the p-menthane halides can be p-menthane-3-halides, and can generally have formula (IV):

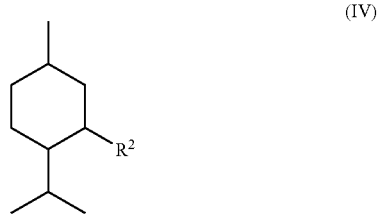

(IV)

wherein:

R² is a halogen or a $C_1$-$C_9$ aliphiatic group comprising at least one halide moiety, wherein the $C_1$-$C_9$ aliphatic group is optionally substituted with at least one $C_1$-$C_{10}$ alkyl, $C_2$-$C_{10}$ alkene, $C_2$-$C_{10}$ alkynyl, and combinations thereof.

In particularly preferred embodiments of the present process, the alicyclic halide compounds are p-menthane halides, including, but not limited to, p-menth-3-yl chloride, p-menth-3-yl bromide, p-menth-3-yl iodide, and mixtures thereof. Additionally, p-menth-3-yl fluoride can be used in the present process. However, if p-menth-3-yl fluoride is used, activated magnesium, such as Rieke magnesium, should also be used.

Carbon Dioxide:

As opposed to conventional Grignard reactions, which require the Grignard reagent to be fully produced first, before reacting the Grignard reagent with carbon dioxide, the current process allows carbon dioxide to be added concurrently to the magnesium, the alicyclic halide compound, the solvent, and the alicyclic Grignard reagent, while the alicyclic Grignard reagent is still being produced, to form at least one alicyclic carboxylate magnesium salt. In preferred embodiments of the present process, the carbon dioxide can be added concurrently to the magnesium, the alicyclic halide compound, the solvent, and the alicyclic Grignard reagent at a rate of about 0.01 to about 1.0 moles/hour, and more preferably at a rate of about 0.05 to about 0.8 moles/hour. In certain preferred embodiments of the present process, the carbon dioxide can be added concurrently to the magnesium, the alicyclic halide compound, the solvent, and the alicyclic Grignard reagent at a rate of at least 0.1 moles/hour, and more preferably at a rate of about 0.1 to about 0.5 moles/hour.

Additionally, the carbon dioxide can be added continuously or semi-continuously, and can be added in gaseous form or solid form (e.g., dry ice). In certain embodiments, if the carbon dioxide is added in gaseous form, the carbon dioxide can be bubbled into the Grignard reaction mixture comprising the magnesium, the alicyclic halide compound, the solvent, and the alicyclic Grignard reagent.

Moreover, in preferred embodiments of the present process, the formation of the alicyclic Grignard reagent can be started first, before the carbon dioxide is concurrently added to the Grignard reaction mixture. According to such embodiments of the present process, the formation of the alicyclic Grignard reagent can be started by reacting magnesium and at least one alicyclic halide compound in at least one solvent. After the formation of the alicyclic Grignard reagent is started, the carbon dioxide can then be added concurrently to the Grignard reaction mixture, while the alicyclic Grignard reagent is still being produced.

Furthermore, in preferred embodiments of the present process, the alicyclic halide compound or compounds can be added continuously or semi-continuously to the Grignard reaction mixture at a rate of about 0.01 to 1.0 moles/hour, more preferably at a rate of about 0.05 to 0.8 moles/hour. In certain preferred embodiments of the present process, the alicyclic halide compound or compounds can be added continuously or semi-continuously to the Grignard reaction mixture at a rate of at least 0.1 moles/hour, and more preferably at a rate of about 0.1 to about 0.5 moles/hour.

With respect to solvents useful for the present process, various solvents can be employed, including the use of a single solvent or multiple solvents. In particular, preferred solvents include, but are not limited to, glycol ethers, including, butyl diglyme (diethylene glycol dibutyl ether), ethyl diglyme (diethylene glycol diethyl ether), ethylene glycol dimethyl ether, and glycerol trimethyl ether; para cymene; tetrahydrofuran; 2-methyl tetrahydrofuran; tetrahydrofurfuryl ethyl ether; tetrahydropyrane; dibutyl ether; anisole; kerosene; benzene; toluene; xylene; n-hexane; cyclohexane; and mixtures thereof. In preferred embodiments of the present process, the solvent or mixture of solvents can comprise a boiling point of at least 65° C. at 1 atmosphere. Additionally, in particularly preferred embodiments of the present process, the solvent or mixture of solvents can comprise a boiling point of at least 150° C. at 1 atmosphere.

In certain embodiments of the present process, the alicyclic Grignard reagent and the alicyclic carboxylate magnesium salt are prepared at a temperature of at least 75° C. In yet additional embodiments of the present process, the alicyclic Grignard reagent and the alicyclic carboxylate magnesium salt are prepared at a temperature of at least 80° C. Further, in yet even additional embodiments of the present process, the alicyclic Grignard reagent and the alicyclic carboxylate magnesium salt are prepared at a temperature of at least 90° C. In particularly preferred embodiments of the present process, the process is carried out at a temperature of at least 75° C. while the magnesium, at least one alicyclic halide compound, and at least one solvent are reacted together. In additional particularly preferred embodiments of the present process, the process is carried out at a temperature of at least 80° C. once at least a portion of the carbon dioxide is concurrently added to the Grignard reaction mixture comprising the magnesium, the alicyclic halide compound, the solvent, and the alicyclic Grignard reagent. Furthermore, in certain particularly preferred embodiments of the present process, the process is carried out at a temperature of at least 90° C. once at least a portion of the alicyclic halide compound and at least a portion of the carbon dioxide are added to the Grignard reaction mixture.

The yields of conversion of at least one alicyclic halide compound to the resultant alicyclic carboxylic acid compound or compounds can be at least about 25% by weight. However, in preferred embodiments of the present process, the yield of conversion of the alicyclic halide compound or compounds to the resultant alicyclic carboxylic acid compound or compounds can be at least about 50% by weight, and more preferably can be at least about 75% by weight.

In addition to at least one solvent, the present process can include any number and amount of additional constituents typically used in conventional Grignard reactions, including, but not limited to, activating agents and entrainments agents. In certain embodiments of the present process, at least one activating agent, at least one entrainment agent, or a combination of at least one activating agent and at least one entrainment agent can be used, and can be added prior to the addition of the alicyclic halide compound or compounds to the magnesium and the solvent. Non-limiting examples of preferred activating agents and entrainment agents include iodine, methyl iodide, and 1,2-dibromo ethane.

Once the alicyclic carboxylate magnesium salt has been formed from the concurrent addition of the carbon dioxide to the Grignard reaction mixture comprising the magnesium, the alicyclic halide compound, the solvent, and the alicyclic Grignard reagent, the alicyclic carboxylate magnesium salt can be hydrolyzed by conventional Grignard reaction techniques, including using water or an acid to liberate the alicyclic carboxylic acid compound. In a preferred embodiment of the present process, the acid used to hydrolyze the alicyclic carboxylate magnesium salt to form the alicyclic carboxylic acid compound is hydrochloric acid.

Additionally, hydrolysis of the alicyclic carboxylate magnesium salt can be performed in the same or different reaction vessel in which the alicyclic carboxylate magnesium salt is prepared. In particularly preferred embodiments of the present process, the alicyclic carboxylate magnesium salt can be hydrolyzed in the same reaction vessel in which the alicyclic carboxylate magnesium salt is prepared. Alternatively, in other preferred embodiments of the present process, the alicyclic carboxylate magnesium salt can be transferred to a separate reaction vessel, whereby the alicyclic carboxylate magnesium salt can be hydrolyzed to form the alicyclic carboxylic acid compound.

EXAMPLES

The following examples are illustrative of preferred processes and compositions, and are not intended to be limitations thereon. All product composition percentages and yields are based on totals equal to 100% by weight, unless otherwise specified.

Test Methods:

Vapor-phase chromatography (VPC) analysis was performed on a Hewlett Packard 6890 having a 30M polar Stabilwax® capillary column at an initial temperature and time of 50° C. and 5 minutes, respectively, and at a rate of 15 degrees per minute, up to a final temperature and time of 225° C. and 15 minutes, respectively. The detector was a flame ionization detector (FID), and the carrier gas was helium.

Example 1 p-Menthane-3-carboxylic acid

Magnesium (15.6 g, 50 mesh), 2-methyl-tetrahydrofuran (103 g), para cymene (50 g), iodine (0.1 g), and ethyl magnesium chloride (4 cc) were added under nitrogen to a 1-liter flask equipped with agitation, addition funnel, off-set adaptor for thermometer, gas addition tube, and condenser. The mixture was stirred for 30 min. at 75° C., and then 1,2,-dibromo ethane (4 cc) was slowly added. p-Menth-3-yl chloride (134 g dissolved in para cymene) was then added at a rate of 33 g/hr (0.21 mole/hr). After approximately ½ of the p-menth-3-yl chloride was added, carbon dioxide was concurrently added by bubbling the carbon dioxide into the mixture at a rate of 7.8 g/hr (0.18 mole/hr), and at a temperature of 80° C. After all of the p-menth-3-yl chloride was added, the temperature was raised to 90° C. to complete carbonation. After carbonation was complete, the resultant mixture was hydrolyzed with aqueous hydrochloric acid having a concentration of 15%. VPC analysis showed a yield of 78.3% by weight of p-menthane-3-carboxylic acid.

Example 2 p-Menthane-3-carboxylic acid

Magnesium (37 g, 50 mesh), butyl diglyme (600 g), and iodine (0.1 g) were added under nitrogen to a 1-liter flask equipped with agitation, addition funnel, off-set adaptor for thermometer, gas addition tube, and condenser. The mixture was stirred for 30 min. at 90° C., and then 1,2,-dibromo ethane (2 cc) was slowly added. p-Menth-3-yl chloride (200 g) was then added at a rate of 50 g/hr (0.32 mole/hr). After approximately ½ of the p-menth-3-yl chloride was added, carbon dioxide was concurrently added by bubbling the carbon dioxide into the mixture at a rate of 15.91 g/hr (0.36 mole/hr), and at a temperature of 90° C. Addition of the carbon dioxide was continued at a temperature of 90° C. until 30 min. after all of the p-menth-3-yl chloride was added. After carbonation was complete, the resultant mixture was hydrolyzed with aqueous hydrochloric acid (1:1 hydrochloric acid/water), and the resultant oil layer was neutralized with trisodium phosphate. VPC analysis showed a yield of 93.18% by weight of p-menthane-3-carboxylic acid.

The present subject matter being thus described, it will be apparent that the same may be modified or varied in many ways. Such modifications and variations are not to be regarded as a departure from the spirit and scope of the present subject matter, and all such modifications and variations are intended to be included with the scope of the following claims.

I claim:

1. A process for preparing at least one alicyclic carboxylic acid compound by Grignard reaction, the process comprising:
    reacting magnesium and at least one alicyclic halide compound in at least one solvent to produce at least one alicyclic Grignard reagent;
    concurrently adding carbon dioxide to the magnesium, the alicyclic halide compound, the solvent, and the alicyclic Grignard reagent, while the alicyclic Grignard reagent is still being produced, to form at least one alicyclic carboxylate magnesium salt; and
    hydrolyzing the alicyclic carboxylate magnesium salt to form the alicyclic carboxylic acid compound;
    wherein the alicyclic Grignard reagent and the alicyclic carboxylate magnesium salt are prepared in a one-pot synthesis.

2. The process of claim 1, wherein the alicyclic carboxylic acid compound is at least one p-menthane derivative.

3. The process of claim 2, wherein the p-menthane derivative is p-menthane-3-carboxylic acid.

4. The process of claim 1, wherein the alicyclic halide compound is at least one p-menthane halide.

5. The process of claim 4, wherein the p-menthane halide is selected from the group consisting of p-menth-3-yl chloride, p-menth-3-yl bromide, p-menth-3-yl iodide, and mixtures thereof.

6. The process of claim 1, wherein the carbon dioxide is concurrently added at a rate of about 0.05 to about 0.8 moles/hour.

7. The process of claim 6, wherein the carbon dioxide is concurrently added at a rate of about 0.1 to 0.5 moles/hour.

8. The process of claim 1, wherein the process yields at least 50% by wt. conversion of the alicyclic halide compound to the alicyclic carboxylic acid compound.

9. The process of claim 1, wherein the process yields at least 75% by wt. conversion of the alicyclic halide compound to the alicyclic carboxylic acid compound.

10. The process of claim 1, wherein the alicyclic halide compound is added to the magnesium and the solvent at a rate of about 0.1 to 0.5 moles/hour.

11. The process of claim 1, wherein the alicyclic Grignard reagent and the alicyclic carboxylate magnesium salt are prepared at a temperature of at least 75° C.

12. The process of claim 1, wherein the alicyclic Grignard reagent and the alicyclic carboxylate magnesium salt are prepared at a temperature of at least 90° C.

13. The process of claim 1, wherein the solvent comprises a boiling point of at least 65° C. at 1 atmosphere.

14. The process of claim 1, wherein the solvent comprises a boiling point of at least 150° C. at 1 atmosphere.

15. The process of claim 1, wherein the process further comprises adding at least one entrainment reagent to the magnesium and the solvent prior to adding the alicyclic halide compound.

16. The process of claim 15, wherein the entrainment reagent is 1,2-dibromo ethane.

* * * * *